United States Patent
Serra Alfaro et al.

(10) Patent No.: US 7,629,499 B2
(45) Date of Patent: Dec. 8, 2009

(54) PROCESS FOR TRANSALKYLATION OF ALKYL-AROMATIC HYDROCARBONS USED IN TWO REACTION ZONES

(75) Inventors: José Manuel Serra Alfaro, Valencia (ES); Avelino Corma, Valence (ES); Emmanuelle Guillon, Vernaison (FR)

(73) Assignee: Institut Francais du Petrole, Malmaison Cedex (FR)

( * ) Notice: Subject to any disclaimer, the term of this patent is extended or adjusted under 35 U.S.C. 154(b) by 783 days.

(21) Appl. No.: 11/269,531

(22) Filed: Nov. 9, 2005

(65) Prior Publication Data

US 2006/0100471 A1    May 11, 2006

(30) Foreign Application Priority Data

Nov. 9, 2004    (FR) .................................. 04 11960

(51) Int. Cl.
*C07C 6/12*    (2006.01)
(52) U.S. Cl. ....................................... 585/475; 585/470
(58) Field of Classification Search ................ 585/475, 585/470
See application file for complete search history.

(56) References Cited

U.S. PATENT DOCUMENTS

| | | | |
|---|---|---|---|
| 4,365,104 A * | 12/1982 | Kaeding ..................... | 585/467 |
| 5,030,787 A | 7/1991 | Absil et al. | |
| 5,942,651 A | 8/1999 | Beech, Jr. et al. | |
| 6,136,290 A * | 10/2000 | Benazzi et al. ............... | 423/705 |
| 6,281,399 B1 * | 8/2001 | Schulz et al. ................ | 585/323 |
| 6,359,184 B1 | 3/2002 | Kato et al. | |

OTHER PUBLICATIONS

UOP TA'C9—3 pages, (2006).

* cited by examiner

*Primary Examiner*—Thuan Dinh Dang
(74) *Attorney, Agent, or Firm*—Millen, White, Zelano & Branigan, P.C.

(57) ABSTRACT

A process for transalkylation of an alkyl-aromatic hydrocarbon feedstock that has at least 9 carbon atoms per molecule that comprises a) the introduction of said alkyl-aromatic hydrocarbon feedstock at the inlet of a first reaction zone where it is brought into contact with at least a first zeolitic catalyst, b) the introduction of at least a portion of the effluent that is obtained from stage a) and a feedstock that contains benzene and/or toluene at the inlet of a second reaction zone that contains at least a second zeolitic catalyst, and c) the separation of at least a portion of the effluent that is obtained from stage b) is described.

19 Claims, No Drawings

PROCESS FOR TRANSALKYLATION OF ALKYL-AROMATIC HYDROCARBONS USED IN TWO REACTION ZONES

This invention relates to the field of the transformation of alkyl-aromatic hydrocarbons containing at least 9 carbon atoms. More specifically, it relates to a process for transalkylation of benzene and/or toluene and alkyl-aromatic hydrocarbons that have at least 9 carbon atoms per molecule to produce xylenes.

The transalkylation reaction generally consists in converting a feedstock that contains toluene and alkyl-aromatic hydrocarbons with at least 9 carbon atoms for the purpose of producing a mixture of xylenes (orthoxylene, metaxylene and paraxylene). Another aromatic compound with 8 carbon atoms, ethylbenzene, is also formed. The paraxylene exhibits a true industrial advantage in particular for the textile industry, and it is suitable for separating other aromatic compounds with eight carbon atoms. Thus, at the outlet of the transalkylation reactor, all of the products that are formed are introduced into a separating column so as to separate the columns with at least six carbon atoms from the lightest compounds. The heaviest fraction is subjected to several separations so as to extract the benzene and the toluene, and then the effluent that consists of compounds with at least eight carbon atoms is introduced into a separating column that makes it possible to recover, at the bottom of the column, a fraction that contains essentially compounds with at least nine carbon atoms and also a portion of orthoxylene, and, at the top of the column, a fraction that is formed by aromatic compounds with eight carbon atoms (xylenes+ethylbenzene), whereby this fraction is then treated in stages of isomerization and separation of paraxylene. The stage for separation of the paraxylene is all the more facilitated as the proportion of ethylbenzene in said fraction that is formed by aromatic compounds with eight carbon atoms is smaller.

The processes for transalkylation of alkyl-aromatic hydrocarbons that are described in the prior art are generally fixed-bed processes. The performance levels of such processes therefore essentially depend on catalytic formulations that are selected as well as the nature of the feedstock and operating conditions.

Numerous transalkylation catalysts have already been described in the prior art and are based on mordenite, ZSM-5, or else based on omega-zeolite.

To upgrade increasingly heavy aromatic feedstocks (having alkyl groups with more than one carbon atom (ethyl, propyl, . . . ), catalytic formulations that are based on composite catalysts have been developed: for example, Patent Application FR-A-2,744,650 describes the use of a composite catalyst for the transalkylation of alkyl-aromatic hydrocarbons based on Mordenite-structural-type zeolites and Mazzite-structural-type zeolites. U.S. Pat. No. 5,942,651 describes a catalytic system that comprises two distinct and separated catalytic compositions, one, zeolite-based, that has a constraint index of between 0.5 and 3 and that contains a noble metal, and the second, zeolite-based, that has a constraint index of between 3 and 12 without added metal. U.S. Pat. No. 5,905,051 discloses a catalytic system that comprises a first catalytic composition based on Beta zeolite that is promoted by a metal and a second catalytic composition based on ZSM-5 zeolite in which a promoter (S, P, Si) is impregnated.

In most of the processes, the aromatic feedstock that is used consists of benzene and/or toluene, on the one hand, and heavy aromatic hydrocarbons that have at least 9 carbon atoms per molecule, on the other hand. The yield of xylenes, produced by such processes, still merits improvement. Also, this invention proposes providing a new transalkylation process that leads to improved catalytic performance levels relative to those obtained by the processes of the prior art, in particular in terms of xylene yield.

SUMMARY AND ADVANTAGE OF THE INVENTION

The object of this invention is a process for transalkylation of an alkyl-aromatic hydrocarbon feedstock that has at least 9 carbon atoms per molecule comprising:
a) Introduction of said alkyl-aromatic hydrocarbon feedstock at the inlet of a first reaction zone where it is brought into contact with at least a first zeolitic catalyst,
b) Introduction of at least a portion of the effluent that is obtained from stage a) and a feedstock that contains benzene and/or toluene at the inlet of a second reaction zone that contains at least a second zeolitic catalyst, and
c) The separation of at least a portion of the effluent that is obtained from stage b).

The process according to this invention proves very effective for the transalkylation of alkyl-aromatic hydrocarbons and preferably for the transalkylation of benzene and/or toluene and $AC_9^+$ alkyl-aromatic hydrocarbons (i.e., with at least 9 carbon atoms per molecule), because it makes it possible to treat feedstocks that contain a large amount of $AC_9^+$ heavy aromatic compounds, whereby these heavy aromatic compounds can contain a large proportion of $AC_{10}^+$. Thus, $AC_9^+$ feedstocks that contain at least 5% and up to 25% by weight, and even more $AC_{10}^+$ can be upgraded. By way of examples, it is possible to cite, in a non-exhaustive manner, dimethylethylbenzenes, diethylbenzenes, propylethylbenzenes, . . . .

It was discovered by the applicant, surprisingly enough, that the introduction of an AC9+ feedstock, lacking in benzene and/or toluene or present in trace state, into a first reaction zone and the introduction of benzene and/or toluene into a second reaction zone, placed downstream from said first zone, leads to an improvement in xylene yield relative to that obtained by the prior processes in which the AC9+ feedstock and the benzene and/or toluene are introduced simultaneously in a mixture in the same feedstock. Furthermore, it was also discovered in a very surprising and advantageous manner that, in comparison to the known processes, the process according to the invention makes it possible to reduce the amount of catalyst that is necessary for carrying out the transalkylation reaction while keeping catalytic performance levels satisfactory, in particular in terms of xylene yield.

DESCRIPTION OF THE INVENTION

The object of this invention is a process for transalkylation of an alkyl-aromatic hydrocarbon feedstock that has at least 9 carbon atoms per molecule comprising:
a) Introduction of said alkyl-aromatic hydrocarbon feedstock at the inlet of a first reaction zone where it is brought into contact with at least a first zeolitic catalyst,
b) Introduction of at least a portion of the effluent that is obtained from stage a) and a feedstock that contains benzene and/or toluene at the inlet of a second reaction zone that contains at least a second zeolitic catalyst, and
c) The separation of at least a portion of the effluent that is obtained from stage b).

The installation that makes it possible to carry out the transalkylation process according to the invention comprises at least two separate reaction zones, each containing at least one zeolitic catalyst. Each of said reaction zones can be included in a single catalytic reactor, the first reaction zone at the inlet of which is introduced said alkyl-aromatic hydrocarbon feedstock that is located upstream from the second reaction zone at the inlet of which are introduced at least a portion of the effluent that exits from said first reaction zone and a feedstock that contains benzene and/or toluene. The introduction of the feedstock that contains benzene and/or toluene can, for example, be done by lateral injection into the reactor in a zone that is located between the first and the second reaction zones. Each of said reaction zones can also be found in a separate catalytic reactor: the first reaction zone at the inlet of which is introduced said alkyl-aromatic hydrocarbon feedstock is then found in a first catalytic reactor and the second reaction zone at the inlet of which are introduced at least a portion of the effluent that exits from said first reaction zone and a feedstock that contains benzene and/or toluene is found in a second catalytic reactor, located downstream from said first reactor and in a series. The introduction of the feedstock that contains benzene and/or toluene can be done by, for example, lateral injection between the first and the second reactors.

The alkyl-aromatic hydrocarbon feedstock that is introduced at the inlet of the first reaction zone contains aromatic compounds that have at least 9 carbon atoms per molecule (AC9+ feedstock). This feedstock is advantageously obtained from a process for the production of aromatic compounds operating in a loop and generating alkyl-aromatic hydrocarbons having at least 9 carbon atoms per molecule as well as by-products. It contains in particular alkyl-aromatic hydrocarbons with 9 carbon atoms such as ethyl toluene and trimethylbenzenes and alkyl-aromatic hydrocarbons with at least 10 carbon atoms. It essentially contains alkyl-aromatic hydrocarbons having at least 9 carbon atoms, advantageously representing at least 90%, preferably at least 95%, by volume of the feedstock, but it can also contain benzene and/or toluene in the trace state (several ppm). Very preferably, it contains only alkyl-aromatic hydrocarbons having at least 9 carbon atoms per molecule.

The feedstock that contains benzene and/or toluene introduced at the inlet of the second reaction zone according to stage b) of the process according to the invention essentially consists of benzene and/or toluene. Advantageously, the benzene and/or the toluene represents at least 80%, preferably at least 90%, by volume of said feedstock. Very preferably, it consists only of benzene and/or toluene and is obtained in general from the distillation of an aromatic fraction that is obtained from catalytic reforming and pyrolysis (steam-cracking) of naphthas. In the case where said feedstock that is introduced at the inlet of the second reaction zone contains benzene and toluene, the benzene/toluene mixture contains for the most part toluene, i.e., at least 50% by volume, preferably at least 65% by volume. Very preferably, said feedstock that is introduced at the inlet of the second reaction zone contains only pure toluene.

According to the invention, the amount of alkyl-aromatic hydrocarbon feedstock that is used for stage a) and the amount of feedstock that contains benzene and/or toluene used for stage b) are such that the mixture of these two feedstocks, without previous transformation, would contain 1 to 99% of AC9+ relative to the total mixture.

For the implementation of the process according to the invention, a first hydrogen flow is introduced at the inlet of said first reaction zone and a second hydrogen flow is introduced at the inlet of said second reaction zone.

According to stage b) of the process according to the invention, the feedstock that contains benzene and/or toluene is introduced at the inlet of the second reaction zone with at least a portion of the effluent that is obtained from stage a). Advantageously, said effluent is mixed at least in part with said feedstock that contains benzene and/or toluene, preferably consisting only of pure toluene, upstream from the second reaction zone so as to constitute the feedstock that is introduced at the inlet of said second reaction zone. Said effluent that is obtained from stage a) of the process according to the invention generally contains alkyl-aromatic hydrocarbons with at least 9 unconverted carbon atoms per molecule as well as benzene, toluene and xylenes produced during stage a). Said effluent that is obtained from stage a) is preferably introduced as a whole at the inlet of the second reaction zone.

The operating conditions (temperature, pressure, flow rate) implemented in stages a) and b) of the process according to the invention are those that are known to one skilled in the art. They can be identical or different in the first and second reaction zones.

In each of the reaction zones, the temperature is between 250 and 650° C. and preferably between 350 and 550° C.; the pressure is between 1 and 6 MPa, and preferably between 2 and 4.5 MPa; the feed volumetric flow rate per reaction zone, expressed by kilogram of feedstock introduced per kilogram of catalyst and per hour, is between 0.05 and 20 $h^{-1}$ and preferably between 0.5 and 10 $h^{-1}$, and a molar ratio of hydrogen to atomic hydrocarbons ($H_2$/aromatic HC) of between 1 and 30 and preferably between 3 and 12 mol/mol. The feed volumetric flow rate in the first reaction zone is defined as WHSV1=(mass flow rate of the alkyl-aromatic hydrocarbon feedstock with at least 9 carbon atoms)/(mass of the first zeolitic catalyst). The feed volumetric flow rate in the second reaction zone is defined as WHSV2=(mass flow rate of the feedstock that contains benzene and/or toluene+mass flow rate of the effluent that is obtained from the first reaction zone)/(mass of the second zeolitic catalyst).

An overall feed volumetric flow rate (WHSV) of between 0.05 and 20 $h^{-1}$ is also defined on the entire first and second reaction zones of the process according to the invention. The overall feed volumetric flow rate WHSV is determined by the formula:

WHSV=(mass flow rate of the feedstock that contains benzene and/or toluene+mass flow rate of the AC9+ feedstock)/(mass of the first zeolitic catalyst+mass of the second zeolitic catalyst). An overall $H_2$/aromatic HC molar ratio is also defined over the entire first and second reaction zones of the process according to the invention as between 1 and 30 and preferably between 3 and 12. This overall $H_2$/aromatic HC molar ratio is determined by the formula: $H_2$/aromatic HC=(number of moles of $H_2$ introduced into the first reaction zone and the second reaction zone)/(number of moles of aromatic hydrocarbons introduced into the first reaction zone and the second reaction zone).

The transalkylation reaction implemented in the first and second reaction zones according to stages a) and b) of the process according to the invention is followed by at least one separation stage c) of at least a portion, preferably the entirety, of the effluent that is obtained from stage b) so as to recover the excess reagents, on the one hand, i.e., the alkyl-aromatic hydrocarbons with at least 9 carbon atoms, benzene and/or toluene, preferably toluene, and xylenes, on the other hand. More specifically, at the outlet of the second reaction zone used for the implementation of stage b) of the process according to the invention, in general the product that is obtained is fractionated so as to collect, separately, a first effluent that contains benzene and/or toluene, unconverted, a second effluent that contains aromatic compounds with 8 carbon atoms, in particular xylenes, a third effluent that contains alkyl-aromatic hydrocarbons that have at least 9 carbon atoms, unconverted, and a fourth effluent that contains light paraffins that have 1 to 6 carbon atoms.

According to stages a) and b) of the process according to the invention, the first reaction zone contains at least a first zeolitic catalyst, and the second reaction zone contains at least a second zeolitic catalyst. Such catalysts are known to one skilled in the art for carrying out transformations of hydrocarbons on their surfaces.

Said first zeolitic catalyst and said second zeolitic catalyst that are present respectively in said first reaction zone and said second reaction zone advantageously comprise at least one zeolite of crystalline structure that has, for example, a structure as defined in the classification "Atlas of Zeolite Structure Types" (W. M. Meier, D. H. Olson and Ch. Baerlocher, 5$^{th}$ Revised Edition, 2001, Elsevier) to which this application also refers. The zeolites are classified therein according to the size of their pore or channel openings. Each zeolite that is present in said first zeolitic catalyst and said second zeolitic catalyst comprises at least one element X that is selected from among silicon and germanium and at least one element T that is selected from among aluminum, iron, gallium, boron, titanium, vanadium, zirconium, molybdenum, arsenic, antimony, chromium and manganese.

Said first zeolitic catalyst and said second zeolitic catalyst preferably comprise at least one zeolite that is selected from the group that consists of the zeolites of MOR, BEA, MFI, EUO, FAU, BOG, TON and NES structural type. Among the MOR-structural-type zeolites, the mordenite zeolite is preferred. Among the BEA-structural-type zeolites, the beta zeolite is preferred. Among the MFI-structural-type zeolites, the ZSM-5 zeolite is preferred. Among the EUO-structural-type zeolites, the EU-1 zeolite is preferred. Among the FAU-structural-type zeolites, the Y zeolite and the Y zeolite that is exchanged with rare earths (REY) are preferred. Among the BOG-structural-type zeolites, the boggiste zeolite is preferred. Among the TON-structural-type zeolites, the ZSM-22 zeolite is preferred. Among the NES-structural-type zeolites, the NU-87 zeolite is preferred. As a zeolite in said first and/or second zeolitic catalyst, it is also advantageously possible to select an IM-5 zeolite (FR-A-2,754,809 or U.S. Pat. No. 6,136,290). Advantageously, the zeolites that are present in said first and said second zeolitic catalysts are in acid form.

The zeolites that are present in said first zeolitic catalyst and said second zeolitic catalyst can be calcinated and exchanged by at least one treatment by a solution of at least one ammonium salt so as to obtain the ammonium form of zeolites which, once calcinated, leads to the hydrogen form of said zeolites. Said zeolites are at least in part, preferably virtually entirely, in acid form, i.e., in hydrogen ($H^+$) form. The Na/T atomic ratio is generally less than 10% and preferably less than 5% and even more preferably less than 1%.

According to an embodiment of the invention, said first zeolitic catalyst and said second zeolitic catalyst comprise one and the same zeolite, i.e., a zeolite of the same structural type and that has the same chemical composition of their crystalline framework (same X/T ratio where X and T have the same definitions as above) in said first zeolitic catalyst and said second zeolitic catalyst. Preferably, it is an MFI-structural-type zeolite, in particular the ZSM-5 zeolite.

According to another embodiment of the invention, said first zeolitic catalyst differs from said second zeolitic catalyst. For example, said first zeolitic catalyst can comprise a zeolite that has a structural type and/or a chemical composition of its crystalline framework (X/T ratio) that is different from the one in said second zeolitic catalyst. Very preferably, the first zeolitic catalyst comprises at least one zeolite that has channels whose openings are defined by a ring with 10 oxygen atoms (opening of 10 MR) and the second zeolitic catalyst comprises at least one zeolite that has channels whose openings are defined by a ring with 10 oxygen atoms (opening of 10 MR), and at least one zeolite that has at least channels or lateral pockets whose openings are defined by a ring with 12 oxygen atoms (opening of least 12 MR). According to the invention, the zeolite channels that have an opening of 10 MR, referred to in the rest of the description below as 10 MR zeolites, are the main channels that empty directly outside of said zeolites. The zeolite that has an opening of at least 12 MR, referred to in the description below as an at least 12 MR zeolite, has at least either 12 MR primary channels that empty directly outside of said zeolite or 12 MR secondary channels that are only accessible by primary channels that have openings other than 12 MR or else lateral pockets ("side pockets"), whose openings are defined by a ring with 12 oxygen atoms. The 10 MR zeolites in said first and second zeolitic catalysts and the at least 12 MR zeolite that is present in said second zeolitic catalyst comprise at least one element X and at least one element T, where X and T have the same definitions as those given above in the description of this invention. Advantageously, X is silicon, and T is aluminum. They are preferably virtually entirely in acid form.

The 10 MR zeolite that is present in the first zeolitic catalyst and the second zeolitic catalyst used for the implementation of stages a) and b) of the process according to the invention is characterized by an Si/Al ratio of between 2 and 250, preferably between 5 and 150, and very preferably between 10 and 80. The sodium content is less than 0.1% by weight, preferably less than 0.05% by weight relative to the total weight of dry zeolite. All of the zeolites that have channels whose openings are defined by a ring with 10 oxygen atoms (10 MR) and that are known in the prior art are suitable for implementation of said first and second zeolitic catalysts. The preferred 10 MR zeolites are selected from among the ZSM-5, IM-5 and ZSM-22 zeolites. The IM-5 zeolite is known by one skilled in the art as being able to be assimilated in a zeolite that has channels whose openings are defined by a ring with 10 oxygen atoms (J. Catal 189 (2000) 382-394, A. Corma et al). These 10 MR zeolites that are described above and their method of preparation are well known to one skilled in the art.

The at least 12 MR zeolite that is present in the second zeolitic catalyst used for the implementation of stage b) of the process according to the invention is characterized by an Si/Al ratio of between 2 and 250, preferably between 5 and 150, and very preferably between 10 and 80. The sodium content is less than 0.1% by weight, preferably less than 0.05% by weight relative to the total weight of dry zeolite. All of the zeolites that have at least channels (primary or secondary) or lateral pockets whose openings are defined by a ring with 12 oxygen atoms (12 MR) and that are known in the prior art are suitable for the implementation of said second zeolitic catalyst. The zeolites with at least 12 MR, preferred within the framework of this invention, are selected from among the beta, Y, mordenite, NU-87, ITQ-23, and EU-1 zeolites and boggsite. The NU-87 zeolite, of the NES structural type, has primary channels of 10 MR and also secondary channels of 12 MR that are accessible by the channels of 10 MR, as described in the book "Synthesis of Microporous Materials," Volume 1, Ed. M. L. Occelli and H. E. Robson, Chap. 24 (Casci, J. L. et al.). The boggsite has primary channels of 10 MR and 12 MR. The EU-1 zeolite has primary channels of 10 MR and lateral pockets ("side pockets") of 12 MR. These zeolites and their method of preparation are well known to one skilled in the art. The ITQ-23 zeolite is described in "A Study of Cyclohexylpyrrolidine-Derived Quaternary Organic Cations as Structure Directing Agents for Synthesis of Zeolites," A. Corma, I. Gimenez, S. Leiva, F. Rey, M. J. Sabater, G. Sastre, S. Valencia, "Abstracts of 14$^{th}$ Int. Zeolite Conference," (Eds. E. van Stee, L. H. Callanan, and M. Claeys), Apr. 25-30, 2004, Cape Town, South Africa.

Concerning said second zeolitic catalyst that is used in stage b) of the process according to the invention and in the case where it comprises at least one 10 MR zeolite and at least one zeolite of at least 12 MR, the distribution between the two zeolites (10 MR zeolite and an at least 12 MR zeolite) is such that the content of zeolite(s) selected from the group that is formed by the 10 MR-type zeolites can vary from 1% to 99%, preferably from 5 to 95%, and even more preferably can vary between 10 and 90% in relative percentages of all of the zeolites that are introduced in the second catalyst. Likewise, the content of an at least 12 MR zeolite varies from 1% to 99%, preferably from 5 to 95%, and even more preferably varies between 10 and 90%, in relative percentages, of all of the zeolites introduced into the second catalyst.

The Si/Al ratios of the 10 MR zeolites and the at least 12 MR zeolites described above are those that are obtained at the end of the synthesis of said zeolites or else obtained after post-synthesis dealuminification treatments that are well known to one skilled in the art, such as, and non-exhaustively, the hydrothermal treatments that may or may not be followed by acid attacks or else direct acid attacks by solutions of mineral or organic acids.

The Si/Al ratio of the 10 MR zeolites and the at least 12 MR zeolites that are part of the composition of said first and second zeolitic catalysts as well as the chemical composition of the samples are determined by X fluorescence and atomic absorption.

It is also possible to consider using a catalyst that comprises a 10 MR zeolite and an at least 12 MR zeolite as a first zeolitic catalyst, and a catalyst comprising a 10 MR zeolite as a second zeolitic catalyst.

The first zeolitic catalyst and/or the second zeolitic catalyst that are used for the implementation of stages a) and b) of the process according to the invention advantageously comprises/comprise at least one metal. Said metal is selected from the group that consists of the metals of groups IIIA, VIB, VIIB and VIII, preferably with a content of between 0.01 and 5% by weight relative to the total weight of the zeolitic catalyst. Among the metals of group IIIA, gallium is preferred. Among the metals of group VIB, molybdenum is preferred. Among the metals of group VIIB, rhenium is preferred. Among the metals of group VIII, nickel is preferred. Very advantageously, the preferred metal among the metals of groups IIIA, VIB, VIIB and VIII is rhenium. Said metal can be present either in the composition of the first zeolitic catalyst or in the composition of the second zeolitic catalyst or else in the composition of the first and second zeolitic catalysts. In stage a) of the process according to the invention, it is very advantageous to use a first zeolitic catalyst that comprises at least a first metal that is selected from the list cited above, and in stage b) of the process according to the invention, it is very advantageous to use a second zeolitic catalyst that comprises at least a second metal that is selected from the list that is cited above and that is different from said first metal. Said first zeolitic catalyst and/or said second zeolitic catalyst used for the implementation of stages a) and b) of the process according to the invention also optionally comprises/comprise at least one metal of group IVA, preferably tin, with a content of advantageously between 0.01 and 5% and preferably between 0.5 and 3% by weight relative to the total weight of the catalyst.

The zeolitic catalysts that are used for the implementation of the process according to the invention are shaped. The shaping can be carried out with matrices other than alumina, such as, for example, magnesia, amorphous silica-aluminas, natural clays (kaolin, bentonite, sepiolite, attapulgite), silica, titanium oxide, boron oxide, zirconia, aluminum phosphates, titanium phosphates, zirconium phosphates, carbon and mixtures thereof. It is preferred to use matrices containing alumina, in all of these forms that are known to one skilled in the art, and even more preferably gamma-alumina. It is also possible advantageously to use mixtures of alumina and silica, mixtures of alumina and silica-alumina. Techniques other than extrusion, such as pelletizing or tabletting, can be used for the shaping.

The zeolitic catalysts that are used for the implementation of the process according to the invention are shaped in the form of grains of different shapes and sizes. They are used in general in the form of cylindrical or multilobar extrudates, such as bilobar, trilobar, or multilobar extrudates of straight or twisted shape, but optionally can be manufactured and used in the form of crushed powder, tablets, rings, balls, or wheels.

The metal/metals present in the composition of the first and/or the second zeolitic catalyst(s) can be deposited on the zeolite or on the matrix of the zeolitic catalyst concerned. For the deposition of metal on the zeolite, in general the cation exchange technique, the dry impregnation technique or the co-precipitation technique is used. For the deposition of metal no longer directly on the zeolite but on the porous mineral matrix (before or after the shaping), in general the anion exchange technique is used. In the case where at least one of the zeolitic catalysts contains several metals, the latter can be introduced either all in the same way or by different techniques, before or after shaping and in any order. In the case where the technique used is that of ion exchange (anion or cation), several successive exchanges may be necessary for introducing the required amounts of metals.

The sources of metals of group VIII that can be used are well known to one skilled in the art. For example, nitrates, sulfates, phosphates, halides, for example chlorides, bromides, and fluorides, and carboxylates, for example acetates and carbonates, will be used. In the case of nickel, it is possible preferably to use nickel nitrate $Ni(NO_3)_2$. The sources of metals of group VIIB that can be used are also well known to one skilled in the art. In the case of rhenium, a complex of ammonium perrhenate $(NH_4)ReO_4$ or perrhenic acid is usually used. The sources of metals of group IIIA that can be used are also well known to one skilled in the art. In the case of gallium, gallium nitrate $Ga(NO_3)_3$ is preferred. The sources of metals of group VIB that can be used are also well known to one skilled in the art. In the case of molybdenum, it is possible to use molybdic acids and their salts, in particular the ammonium salts such as ammonium molybdate, ammonium heptamolybdate as well as phosphomolybdic acid. Ammonium heptamolybdate $(NH_4)_6Mo_7O_{24}$ is preferably used. The deposition of metal or metals of groups IIIA, VIB, VIIB and VIII and optionally group IVA is followed in general by a calcination in air or oxygen, usually between 300 and 600° C. for 0.5 to 10 hours, preferably between 350° C. and 550° C. for 1 to 4 hours. It is possible then to initiate a reduction in hydrogen, generally at a temperature of between 300 and 600° C. for 1 to 10 hours; preferably the operation will be performed between 350° C. and 550° C. for 2 to 5 hours.

According to the embodiment of the invention described above that consists in using, in stage a) of the process according to the invention, at least a first zeolitic catalyst that comprises at least one 10 MR zeolite, and, in stage b) of the process according to the invention, at least a second zeolitic catalyst that comprises at least one 10 MR zeolite and at least one at least 12 MR zeolite, three methods for preparation of the second zeolitic catalyst are provided below. According to a first preparation variant of said second zeolitic catalyst, prior to the shaping thereof, at least one of the zeolites described above and included in said second catalyst is subjected to the deposition of at least one metal that is selected from the group that consists of the metals of groups IIIA, VIB, VIIB and VIII. Preferably, at least one 10 MR zeolite is subjected to the deposition of at least one metal that is selected from the group that consists of the metals of groups IIIA, VIB, VIIB and VIII. It is also possible that the 10 MR zeolite is subjected to the deposition of a metal that is selected from the group that consists of the metals of groups IIIA, VIB, VIIB and VIII and that the at least 12 MR zeolite is subjected to the deposition of another metal that is selected from the group that consists of the metals of groups IIIA, VIB, VIIB and VIII. Advantageously, when said second zeolitic catalyst comprises at last one metal that is selected from the group that consists of the metals of groups IIIA, VIB, VIIB and VIII and at least one metal that is selected from the group IVA, the 10 MR zeolite is subjected to the deposition of the metal that is selected from the group that consists of the metals of groups IIIA, VIB, VIIB and VIII and the at least 12 MR zeolite is subjected to the deposition of the metal that is selected from the group that consists of the metals of group IVA. The zeolites that are thus loaded with metals are mixed. The mixing of these zeolites, which are then in the powder state, is carried out by all of the techniques for mixing powders that are known to one skilled in the art. Once the mixing of zeolite powders, loaded with metals, is carried out, the mixture is shaped by any technique that is known to one skilled in the art. It is possible in particular to be mixed with a porous mineral matrix, generally amorphous, for example with a moist powder of alumina gel. The mixture is then shaped, for example by extrusion through a die, by pelletizing or by tabletting. The porous mineral matrix is of the same type as the one described above in this description. After the shaping stage, the product that is obtained is subjected to a drying stage and then to a calcination stage.

According to a second preparation variant of said second zeolitic catalyst, at least one metal that is selected from the group that consists of the metals of groups IIIA, VIB, VIIB and VIII and optionally at least one metal that is selected from the group IVA is (are) deposited on the substrate after the shaping of 10 MR zeolites and at least 12 MR zeolites, which are free of metals, by any process that is known to one skilled in the art and that makes possible the deposition of metal on zeolites. The mixing of zeolites (free of metals) with at least one porous mineral matrix after shaping, drying and calcination is referred to by the term "substrate." The substrate of said second zeolitic catalyst that is used in stage b) of the process according to the invention generally contains the following contents of matrix and zeolites:

- 5 to 95% by weight, preferably 10 to 90% by weight, more preferably 15 to 85% by weight, and very preferably 20 to 80% by weight of zeolites such that at least one zeolite is selected from among the 10 MR zeolites and at least one zeolite is selected from among the at least 12 MR zeolites,
- 5 to 95%, preferably 10 to 90%, more preferably 15 to 85%, and very preferably 20 to 80% by weight of at least one amorphous or poorly crystallized oxide-type porous mineral matrix.

According to a third preparation variant of said second zeolitic catalyst, each zeolite is shaped independently with a binder. The mixing of zeolites can be carried out after shaping (extrudates or grains). The metals are deposited before or after mixing shaped zeolites, preferably before. A different metal thus can be deposited on the two shaped zeolites.

In a general manner, the preparation of the first and second zeolitic catalysts generally ends by a calcination, preferably under a stream of air, so-called final calcination, usually at a temperature of between 300 and 600° C., preferably preceded by drying, for example in an oven, at a temperature of generally between ambient temperature and 250° C., preferably between 40 and 200° C. Said drying stage is preferably conducted during the rise in temperature necessary to carry out said calcination. It is then possible to initiate a reduction under hydrogen, generally at a temperature of between 300 and 600° C., preferably between 350 and 550° C., and for a period of between 1 and 10 hour(s), and preferably between 2 and 5 hours. Such a reduction may have taken place ex situ or in situ, relative to the site of use of said first and second zeolitic catalysts.

Said first and/or second zeolitic catalyst(s) that are used for the implementation respectively of stages a) and b) of the process according to the invention optionally can contain sulfur. In this case, the sulfur is introduced onto the zeolitic catalyst(s) concerned, shaped, calcined, containing the element or elements cited above, either in situ before the catalytic reaction, or ex situ. The sulfurization is carried out by using all of the sulfurizing agent that is well known to one skilled in the art, such as, for example, dimethyl disulfide or hydrogen sulfide. The optional sulfurization takes place after the reduction. In the case of an in situ sulfurization, the reduction, if the catalyst was not previously reduced, takes place before the sulfurization. In the case of an ex situ sulfurization, the reduction and then the sulfurization are carried out.

The following examples illustrate this invention without thereby limiting its scope.

EXAMPLE 1

Preparation of Catalysts Based on 10 MR Zeolites, Based on at Least 12 MR Zeolites and Based on a 10 MR Zeolite and an at Least 12 MR Zeolite The zeolites that are used to prepare the different catalysts that are used to implement the process according to the invention are presented in Table 1 with their composition (Si/Al atomic ratio measured by X fluorescence (FX)) and their residual sodium content. The five zeolites that are concerned are in acid form.

The beta, mordenite, and ZSM-5 zeolites are commercial zeolites (Zeolyst).

The NU-87 zeolite was synthesized according to European Patent Application EP-A-0,377,291 or Patent EP-B-0,378, 916. The starting zeolite has an overall Si/Al atomic ratio that is equal to 17.2 and a content by weight of sodium that is equal to 1256 ppm. This NU-87 zeolite first undergoes a so-called dry calcination at 550° C. under a stream of air and nitrogen for 6 hours. Then, the solid that is obtained is subjected to an ion exchange in a 10N $NH_4NO_3$ solution at about 100° C. for 4 hours. The NU-87 zeolite is then subjected to a treatment by a 7N nitric acid solution, at about 100° C., for 5 hours. Volume V of the engaged nitric acid solution (in ml) is equal to 10× weight P of the dry NU-87 zeolite (V/P=10). This treatment by a 7N nitric acid solution is carried out a second time under the same operating conditions. At the end of these treatments, the zeolite that is obtained is found in its H shape and has an overall atomic Si/Al ratio that is equal to 33.3, and an Na content of 10 ppm.

The ITQ-23 zeolite is synthesized according to the method that is described by A. Corma et al. in "Abstracts of 14th Int. Zeolite Conference," (Eds. E. van Stee, L. H. Callanan and M. Claeys), Apr. 25-30, 2004, Cape Town, South Africa.

TABLE 1

10 MR Zeolites and At Least 12 MR Zeolites

| Zeolites | Si/Al (FX) | Na (ppm) | Type |
|---|---|---|---|
| Beta | 12.5 | 87 | 12 MR |
| ZSM-5 | 17.5 | 132 | 10 MR |
| Mordenite | 10 | 109 | 12 MR |
| ITQ-23 | 20 | 19 | 10 & 12 MR |
| NU-87 | 33.3 | 10 | 10 & 12 MR |

The zeolites are then shaped by extrusion with an alumina gel so as to obtain, after drying at 120° C. for one night and calcination under dry air at 500° C. for 4 hours, the substrate that contains 80% by weight of zeolite and 20% by weight of alumina. The zeolitic portion consists of a single zeolite (10 MR or 12 MR) or a mechanical mixture of two different zeolites, carried out after shaping.

The zeolitic substrate that comprises a zeolite or a mixture of two different zeolites is subjected to a dry impregnation by a metallic precursor solution (ammonium perrhenate for rhenium, ammonium heptamolybdate for molybdenum, gallium nitrate for gallium) so as to deposit a targeted metal percentage. The moist solid is then dried at 120° C. for 12 hours and calcined under a flow of dry air at the temperature of 500° C. for one hour. The composition of the catalysts obtained is presented in Table 2.

TABLE 2

Catalysts That Contain Either a 10 MR Zeolite or an At Least 12 MR Zeolite or a 10 MR Zeolite or an At Least 12 MR Zeolite

| Catalyst | % Al2O3 | Zeolite(s) | Ratio of Zeolites | % Metal |
|---|---|---|---|---|
| A | 20 | ZSM-5 | 100 | 0.3% Re |
| B | 20 | Mordenite | 100 | 0.3% Mo |
| C | 20 | NU-87 | 100 | 0.3% Re |
| D | 20 | Beta | 100 | 0.3% Re |
| E | 20 | Beta + ZSM-5 | 75/25 | 0.5% Re |
| F | 20 | NU-87 + ZSM-5 | 75/25 | 0.25% Re |
| G | 20 | ITQ-23 + ZSM-5 | 75/25 | 0.25% Ga |

EXAMPLE 2

Catalytic Performance Levels of Zeolitic Catalysts Used for Carrying Out the Transalkylation of an AC9+ Feedstock in a Single Catalytic Reactor Equipped with a Single Reaction Zone (For Comparison)

A catalyst of mass m1 is prepared by carrying out a mechanical mixing that consists of 50% by weight of catalyst A and 50% by weight of a second catalyst (catalyst D or catalyst C). Catalysts A, C and D as well as the catalysts that result from the mixing of A and C and the mixing of A and D are reduced in advance under hydrogen at 450° C. for 2 hours.

The catalyst that results from the mechanical mixing of catalyst A and catalyst C is introduced into a catalytic reactor that is equipped with a single reaction zone. A feedstock that consists of 50% toluene, 16% ethyl toluene, 28% trimethylbenzene and 6% aromatic compounds with at least 10 carbon atoms is introduced at the inlet of the catalytic reactor.

The catalytic tests are carried out under the following operating conditions:

Temperature: 400° C.
Total pressure: 25 bar
$H_2$/HC=8.5 mol/mol (HC refers to all of the aromatic hydrocarbons initially introduced)
WHSV=4 $h^{-1}$ (feedstock mass per catalyst mass and per hour)

This test is reproduced by using a catalyst that results from the mechanical mixing of catalyst A and catalyst D as a catalyst in the reaction zone. The results are provided in the table below.

| | Example | |
|---|---|---|
| | 2.1 | 2.2 |
| Catalyst | 50% A + 50% D | 50% A + 50% C |
| Overall Conversion (%) | 56.1 | 52.3 |
| Xylene Yield (%) | 33.0 | 26.3 |

EXAMPLE 3

Catalytic Performance Levels of Zeolitic Catalysts that are Used to Carry Out the Transalkylation of an AC9+ Feedstock in Two Catalytic Reactors that are Each Equipped with a Reaction Zone (According to the Invention)

A first zeolitic catalyst with mass m'1 is introduced into the first catalytic reactor and a second zeolitic catalyst with mass m'2 is introduced into the second catalytic reactor, placed downstream and in a series from the first reactor. The proportions of m'1 relative to m1 and those of m'2 relative to m1 are provided in the table below, whereby m1 is the mass of the catalyst used in Example 2. For two of the tests carried out in this Example 3, m'1+m'2=m1. For the third test, m'1+m'2<m1.

At the inlet of the first catalytic reactor, an aromatic feedstock that consists of AC9+ hydrocarbons consisting of 32% ethyl toluene, 56% trimethylbenzene and 12% aromatic compounds with at least 10 carbon atoms is introduced. At the inlet of the second catalytic reactor, toluene (same flow rate as the AC9+ feedstock injected at the inlet of the first catalytic reactor) mixed with the effluent that is obtained from the first reactor catalytic is introduced.

The catalytic tests are carried out under the following operating conditions:

Temperature: 400° C. in each of the reactors
Total pressure: 25 bar in each of the reactors
$H_2$/Aromatic HC=8.5 mol/total mol
The WHSV is provided by the formula=(mass flow rate of toluene+mass flow rate of AC9+)/(m'1+m'2)

| | Example | | |
|---|---|---|---|
| | 3.1 | 3.2 | 3.3 |
| 1st Zeolitic Catalyst | A | A | A |
| 2nd Zeolitic Catalyst | E | F | E |

-continued

| | Example | | |
|---|---|---|---|
| | 3.1 | 3.2 | 3.3 |
| m'1/m1 Ratio | m'1 = ⅓ m1 | m'1 = ⅓ m1 | m'1 = ¼ m1 |
| m'2/m1 Ratio | m'2 = ⅔ m1 | m'2 = ⅔ m1 | m'2 = ½ m1 |
| Overall Conversion (%) | 52.2 | 49.3 | 51.9 |
| Xylene Yield (%) | 34.4 | 32.7 | 33.1 |
| WHSV (h$^{-1}$) | 4 | 4 | 5.3 |

The comparison of Examples 2.1 and 3.1 shows that for the same catalytic composition (ZSM-5 and beta zeolites), the same amount (m'1+m'2=1) and the same proportion of zeolites (50% by weight of ZSM-5 zeolite and 50% by weight of beta zeolite), the xylene yield is essentially increased when the toluene is introduced, not mixed with the AC9+ feedstock in a single reaction zone, but at the inlet of a second reaction zone placed downstream from a first reaction zone at the inlet of which the AC9+ feedstock is introduced. This advantageous effect on the xylene yield is also observed by comparing Examples 2.2 and 3.2. Furthermore, the comparison of Examples 2.1 and 3.3 shows that the xylene yield is maintained when two reaction zones are used according to the invention whereas the total amount of zeolites is smaller (m'1+m'2<m1), which thus makes it possible to reduce the necessary amount of zeolitic catalysts when a defined performance level is sought.

EXAMPLE 4

Catalytic Performance Levels of Zeolitic Catalysts Used to Carry Out the Transalkylation of an AC9+ Feedstock in Two Catalytic Reactors that are Each Equipped with a Reaction Zone (According to the Invention)

A first zeolitic catalyst with mass m"1 is introduced into the first catalytic reactor, and a second zeolitic catalyst with mass m"2 is introduced into the second catalytic reactor, placed downstream and in a series from the first reactor.

An aromatic feedstock that consists of AC9+ hydrocarbons that consists of 32% ethyl toluene, 56% trimethylbenzene and 12% aromatic compounds with at least 10 carbon atoms is introduced at the inlet of the first catalytic reactor. Toluene (same flow rate as the AC9+ feedstock that is injected at the inlet of the first catalytic reactor) mixed with the effluent that is obtained from the first catalytic reactor is introduced at the inlet of the second catalytic reactor.

The catalytic tests are carried out under the following operating conditions:
Temperature: 400° C. in each of the reactors
Total pressure: 25 bar in each of the reactors
H$_2$/Aromatic HC=8.5 mol/total mol
The WHSV is given by the formula=(mass flow rate of toluene+mass flow rate of AC9+)/(m"1+m"2)

| | Example | | |
|---|---|---|---|
| | 4.1 | 4.2 | 4.3 |
| 1$^{st}$ Zeolitic Catalyst | A | A | A |
| 2$^{nd}$ Zeolitic Catalyst | B | G | C |
| Overall Conversion | 54.8 | 52.9 | 53.1 |

-continued

| | Example | | |
|---|---|---|---|
| | 4.1 | 4.2 | 4.3 |
| (%) | | | |
| Xylene Yield (%) | 31.8 | 32.4 | 29.5 |
| WHSV (h$^{-1}$) | 4 | 4 | 4 |

The invention claimed is:

1. A process producing xylenes by transalkylation of an alkyl-aromatic hydrocarbon feedstock having at least 9 carbon atoms per molecule and being devoid of benzene and toluene except for possible trace amounts, which process consists essentially of:
   a) a stage (a) introducing said alkyl-aromatic hydrocarbon feedstock at the inlet of a first reaction zone where it is brought into contact with at least a first zeolitic catalyst in the presence of hydrogen to produce by transalkylation, an effluent containing xylenes, benzene and toluene,
   b) in a separate stage (b) introducing at least a portion of resultant effluent obtained from stage a) and a feedstock that consists essentially of benzene and/or toluene to the inlet of a second transalkylation reaction zone that contains hydrogen and at least a second zeolitic catalyst, to form additional xylenes and
   c) separating xylenes from at least a portion of resultant effluent obtained from stage b).

2. A process according to claim 1, in which the feedstock that is introduced at the inlet of said second reaction zone contains essentially only toluene.

3. A process according to claim 1 conducted under operating conditions in said first reaction zone and said second reaction zone such that the temperature is between 250 and 650° C., the pressure is between 1 and 6 MPa, the feed volumetric flow rate is between 0.05 and 20 h$^{-1}$, and the H$_2$/aromatic hydrocarbon molar ratio is between 1 and 30.

4. A process according to claim 1, in which said first zeolitic catalyst and said second zeolitic catalyst comprise at least one zeolite that is selected from the group that consists of the zeolites of the MOW BEA, MFI, EUO, FAU, BOG, TON and NES structural type.

5. A process according to claim 1, in which said first zeolitic catalyst and/or said second zeolitic catalyst comprise at least one IM-5 zeolite.

6. A process according to claim 1, in which said first zeolitic catalyst and said second zeolitic catalyst comprise one and the same zeolite.

7. A process according to claim 6, in which said zeolite is an MFI-structural-type zeolite.

8. A process according to claim 1, in which said first zeolitic catalyst differs from said second zeolitic catalyst.

9. A process according to claim 8, in which said first zeolitic catalyst comprises at least one zeolite having channel openings defined by a ring with 10 oxygen atoms, and said second zeolitic catalyst comprises at least one zeolite having channel openings defined by a ring with 10 oxygen atoms and at least one zeolite having at least channels or lateral pockets whose openings are defined by a ring with 12 oxygen atoms.

10. A process according to claim 9, in which the zeolite that has channels whose openings are defined by a ring with 10 oxygen atoms is selected from the ZSM-5, IM-5 and ZSM-22 zeolites, and the zeolite that has at least channels or lateral pockets whose openings are defined by a ring with 12 oxygen atoms is selected from the beta, Y, mordenite, NU-87, ITQ-23, and EU-1 zeolites and boggsite.

11. A process according to claim 1, in which said first zeolitic catalyst and/or said second zeolitic catalyst comprises/comprise at least one metal that is selected from the group that consists of the metals of groups IIIA, VIB, VIIB and VIII.

12. A process according to claim 11, in which the metal is rhenium.

13. A process according to claim 1, in which in stage a), said first zeolitic catalyst comprises at least a first metal selected from the group that consists of the metals of groups IIIA, VIB, VIIB and VIII is, and in stage b), said second zeolitic catalyst comprises at least a second metal, different from said first metal, and is selected from the group that consists of the metals of groups IIIA, VIB, V1IB and VIII.

14. A process according to claim 1, in which said first zeolitic catalyst and/or said second zeolitic catalyst contain(s) sulfur.

15. A process according to claim 4, in which the feedstock that is introduced at the inlet of said second reaction zone contains only toluene.

16. A process according to claim 14, in which the feedstock that is introduced at the inlet of said second reaction zone contains only toluene.

17. A process according to claim 1, wherein the alkylaromatic feedstock to stage (a) contains less than trace amounts in several parts per million of benzene and/or toluene.

18. A process according to claim 1, wherein the feedstock that is introduced into the second stage contains at least 80% by volume of benzene/toluene.

19. A process according to claim 1, wherein the feedstock that is introduced into the second stage contains at least 90% by volume of benzene/toluene.

* * * * *

UNITED STATES PATENT AND TRADEMARK OFFICE
CERTIFICATE OF CORRECTION

PATENT NO. : 7,629,499 B2 Page 1 of 1
APPLICATION NO. : 11/269531
DATED : December 8, 2009
INVENTOR(S) : Serra Alfaro et al.

It is certified that error appears in the above-identified patent and that said Letters Patent is hereby corrected as shown below:

Column 14, line 44 reads "the zeolites of the MOW, BEA, MFI, EUO, FAU, BOG, TON" should read -- the zeolites of the MOR, BEA, MFI, EUO, FAU, BOG, TON --.

Column 15, line 16 reads "consists of the metals of groups IIIA, VIB, V1IB and VIII." should read -- consists of the metals of groups IIIA, VIB, VIIB and VIII. --.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,629,499 B2 Page 1 of 1
APPLICATION NO. : 11/269531
DATED : December 8, 2009
INVENTOR(S) : Serra Alfaro et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1064 days.

Signed and Sealed this

Second Day of November, 2010

David J. Kappos
*Director of the United States Patent and Trademark Office*